United States Patent
Azzaoui et al.

(10) Patent No.: US 7,754,896 B2
(45) Date of Patent: Jul. 13, 2010

(54) INDOL-ALANINE DERIVATIVES AS SELECTIVE S1P4-AGONISTS

(75) Inventors: Kamal Azzaoui, Basel (CH); Rochdi Bouhelal, Buschwiller (FR); Peter Buehlmayer, Arlesheim (CH); Danilo Guerini, Reinach (CH); Manuel Koller, Schliern (CH)

(73) Assignee: Novartis AG, Basel (CH)

( * ) Notice: Subject to any disclaimer, the term of this patent is extended or adjusted under 35 U.S.C. 154(b) by 897 days.

(21) Appl. No.: 10/586,422

(22) PCT Filed: Jan. 20, 2005

(86) PCT No.: PCT/EP2005/000541
§ 371 (c)(1),
(2), (4) Date: Sep. 18, 2006

(87) PCT Pub. No.: WO2005/070886
PCT Pub. Date: Aug. 4, 2005

(65) Prior Publication Data
US 2009/0023797 A1    Jan. 22, 2009

(30) Foreign Application Priority Data
Jan. 21, 2004    (GB) ................... 0401332.2

(51) Int. Cl.
     C07D 209/04    (2006.01)
     A01N 43/38    (2006.01)
(52) U.S. Cl. ............................. 548/491; 514/419
(58) Field of Classification Search ............... 548/491; 514/419
See application file for complete search history.

(56) References Cited
FOREIGN PATENT DOCUMENTS
WO    03/062252    7/2003
WO    WO 03/061567    *    7/2003

OTHER PUBLICATIONS

Kubinyi (3D QSAR in Drug Design: Ligand-Protein Interactions and Molecular Similarity, vol. 2-3, Springer, 1998, 800 pages).*

Candelore et al. (Biochemical and Biophysical Research Communications (2002), 297(3), 600-606).*

Candelore et al., "Phytosphingosine 1-phosphate: A high affinity ligand for the S1P4/Edg-6 receptor", Biochemical and Biophysical Research Communications, vol. 297, No. 3, pp. 600-606 (2002).

Brashear et al., Nonpeptide Glycoprotein IIB/IIIA inhibitors: 18.Indole alpha-sulfonamide acids are potent inhibitors of platelet aggregation, Bioorganic and Medicinal Chemistry Letters, vol. 7, No. 21, pp. 2793-2798 (1997).

Takuwa et al., "The Edg family G protein-coupled receptors for lysophospholidpids: their signaling properties and biological activities", Journal of Biochemistry, Japanese Biochemical Society, vol. 131, No. 6, pp. 767-771 (2002).

* cited by examiner

*Primary Examiner*—Rebecca L Anderson
*Assistant Examiner*—Robert Havlin
(74) *Attorney, Agent, or Firm*—Hoxie & Associates LLC

(57) ABSTRACT

The present invention relates to agonists of the S1P4 receptor, which are selective for the S1P4 receptor over one or more of the S1P1, S1P2, S1P3 or S1P5 receptors of at least 10 fold, in particular new indol-alanine derivatives of structure I, process for their production, their uses, in particular in transplantation, and pharmaceutical compositions containing them

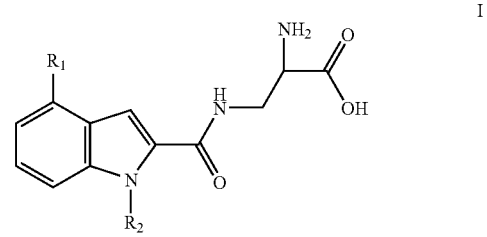

wherein
$R_1$ is phenyl or naphthyl, wherein phenyl is substituted by one or two of halogen, $C_{1-6}$alkyl, $C_{1-6}$alkoxy or phenyl$C_{1-6}$alkyl; and
$R_2$ is hydrogen or $C_{1-6}$alkyl;
in free or salt form.

7 Claims, No Drawings

SEQUENCE LISTING

```
<160> NUMBER OF SEQ ID NOS: 7

<210> SEQ ID NO 1
<211> LENGTH: 49
<212> TYPE: DNA
<213> ORGANISM: Homo sapiens

<400> SEQUENCE: 1
caccatgggc agcttgtact cggagtacct gaaccccaac aaggtccag                    49

<210> SEQ ID NO 2
<211> LENGTH: 27
<212> TYPE: DNA
<213> ORGANISM: Homo sapiens

<400> SEQUENCE: 2
gattcagacc accgtgttgc cctccag                                            27

<210> SEQ ID NO 3
<211> LENGTH: 24
<212> TYPE: DNA
<213> ORGANISM: Homo sapiens

<400> SEQUENCE: 3
caccatggag tcggggctgc tgcg                                               24

<210> SEQ ID NO 4
<211> LENGTH: 31
<212> TYPE: DNA
<213> ORGANISM: Homo sapiens

<400> SEQUENCE: 4
tcagtctgca gccggttctg ataccagagt c                                       31

<210> SEQ ID NO 5
<211> LENGTH: 18
<212> TYPE: DNA
<213> ORGANISM: Homo sapiens
```

```
                                -continued

<400> SEQUENCE: 5
aactgcctgt gcgccttt                                                 18

<210> SEQ ID NO 6
<211> LENGTH: 23
<212> TYPE: DNA
<213> ORGANISM: Homo sapiens

<400> SEQUENCE: 6
gaggatgtag cgcttggagt aga                                           23

<210> SEQ ID NO 7
<211> LENGTH: 20
<212> TYPE: DNA
<213> ORGANISM: Homo sapiens

<400> SEQUENCE: 7
accgctgctc cagccttctg                                               20
```

INDOL-ALANINE DERIVATIVES AS SELECTIVE S1P4-AGONISTS

The present invention relates to organic compounds, a process for their production and pharmaceutical compositions containing them.

In one aspect, the present invention provides a compound which is an agonist of the sphingosine-1-phosphate (S1P4) receptor, wherein the compound possesses selectivity for the S1P4 receptor over one or more of the S1P1, S1P2, S1P3 or S1P5 receptors. S1P receptors are described, for example in WO 03/061567. Preferably the compound is selective for the S1P4 receptor over each of the above S1P receptors. The compound preferably shows a selectivity of at least 10 fold, more preferably 20 fold, most preferably 100 fold for the S1P4 receptor over one or more of the above S1P receptors. Selectivity may be measured by determining the ratio of the $EC_{50}$ of the compound for the S1P4 receptor to the $EC_{50}$ of the compound for S1P1, S1P2, S1P3 or S1P5 receptor. $EC_{50}$ values may be obtained, for example, according to the $GTP\gamma^{35}S$ binding assay or calcium mobilization assay described below. In a further preferred embodiment, the compound also shows an $EC_{50}$ value for the S1P4 receptor of 1 μM or less in the $GTP\gamma^{35}S$ binding assay or calcium mobilization assay.

In a preferred embodiment, the present invention relates to a compound of formula I

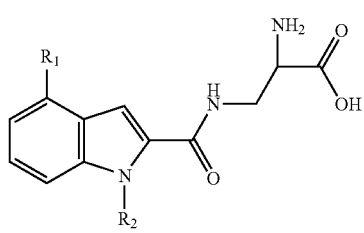

wherein $R_1$ is phenyl or naphthyl, wherein phenyl is substituted by one or two of halogen, $C_{1-6}$alkyl, $C_{1-6}$alkoxy or phenyl$C_{1-6}$alkyl; and $R_2$ is hydrogen or $C_{1-6}$alkyl;

in free or salt form.

Any alkyl moiety may be linear or branched. $C_{1-6}$alkyl is preferably $C_{1-4}$alkyl. $C_{1-6}$alkoxy is preferably $C_{1-4}$alkoxy.

Halogen may be F, Cl, Br, or I.

$R_1$ is preferably a group of formula Ia:

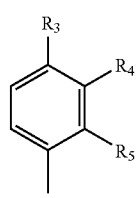

wherein one or two of $R_3$, $R_4$ and $R_5$ is hydrogen; and one or two of $R_3$, $R_4$ and $R_5$ is halogen, $C_{1-6}$alkyl, $C_{1-6}$alkoxy or phenyl$C_{1-6}$alkyl;

or $R_3$ and $R_4$, or $R_4$ and $R_5$, together with the carbon atoms to which they are attached, together form a benzene ring.

In formula I and Ia the following significances are preferred independently, collectively or in any combination or sub-combination:

a) one of $R_4$ or $R_5$ is other than hydrogen, more preferably $R_5$ is other than hydrogen and $R_4$ is hydrogen;

b) $R_4$ or $R_5$ is benzyl, ethyl, butoxy, propyl, isopropyl or chloro, more preferably $R_5$ is one of the aforementioned groups and $R_4$ is hydrogen;

b) $R_3$ is hydrogen or chloro, more preferably hydrogen;

c) $R_2$ is hydrogen or methyl.

The compounds or formula I can also form acid addition salts or inorganic or organic acids, e.g. hydrochloric, hydrobromic or maleic acid. The compounds of formula I can also form cationic salts deriving from the carboxy group, more particularly alkali or alkaline earth metal salts, e.g. sodium, potassium, calcium or magnesium salt, and ammonium salts derived from ammonia or organic amines.

The compounds of formula I contain a chiral centre at the carbon atom bearing the primary amino group. The compound of formula I will therefore exist in two enantiomeric forms. It is to be understood that the present invention encompasses the racemate of the formula I and any enantiomeric form.

The compounds of formula I can also be obtained in the form of their hydrates. The hydrates also form part of the invention.

The present invention also provides a process for the production of the compounds of formula I, which comprises deprotecting a compound of formula II

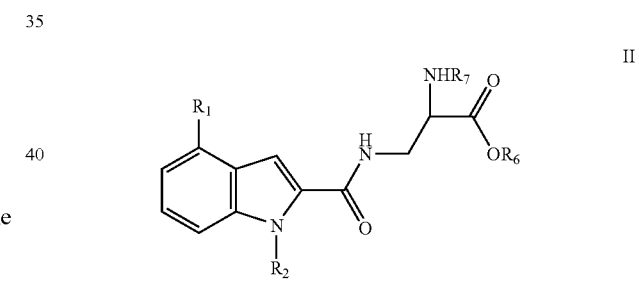

wherein $R_1$ and $R_2$ are as defined above, $R_6$ is $C_{1-6}$alkyl or benzyl, $R_7$ is an amino protecting group, and and if desired converting the compound of formula I into a salt thereof.

The process can be carried out using conventional methods. Examples of suitable amino protecting groups are e.g. as disclosed in "Protective Groups in Organic Synthesis" T. W. Greene, J. Wiley & Sons NY, $2^{nd}$ ed., chapter 7, 1991, and references therein, e.g. acyl, e.g. tert.butyloxycarbonyl, benzyloxycarbonyl, 9-fluorenyl methoxy carbonyl, trifluoroacetyl, trimethylsilylethanesulfonyl and the like. The deprotection can be effected by e.g. hydrogenolysis, when $R_7$ is benzyloxycarbonyl and $R_6$ is benzyl. The reaction can then be carried out in an organic solvent such as tetrahydrofuran, methylene chloride or dioxane at room temperature using palladium-charcoal as catalyst. If $R_6$ is $C_{1-6}$alkyl, the process is conveniently effected in two steps. In the first step the carboxy group of a compound of formula II may be deprotected by mild hydrolysis with e.g. aqueous NaOH or a basic ion-exchange resin in an organic solvent such as tetrahydrofuran, dioxan, methanol or ethanol at room temperature. In the second step the amino group is deprotected with e.g. iodotrimethyllsilane in methylene chloride. If $R_7$ is benzyloxycarbonyl hydrogenolysis can be employed. The two step process is suitably employed when one or two of $R_3$ to $R_5$ are halogen.

The optional formation of a salt may be carried out conventionally.

A racemic mixture of the compound of formula I may be resolved in known manner, for example using an optically active acid as a resolving agent. Alternatively, a pure enantiomeric form may be produced by utilizing optically active starting materials.

Compounds of formula II used as starting material can be prepared by e.g. reacting a compound of formula III

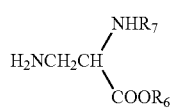

wherein $R_6$ and $R_7$ are as defined above, with a compound of formula IV

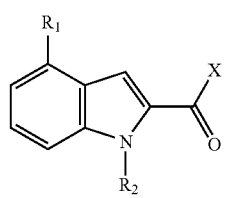

wherein $R_1$ and $R_2$ are as defined above, and X is a leaving group.

The reaction can be effected in conventional manner. For example the reaction can be carried out in an organic solvent such as methylene chloride at a temperature between $-15°$ to $25°$. The leaving group X is e.g. halogen especially chlorine or hydroxy.

Conveniently an acid binding agent, e.g. a tertiary amine such as pyridine, is present.

Insofar as the production of the starting materials for the above processes is not particularly described, these may be produced in analogous manner to known compounds or the processes described herein.

In the following Examples all temperatures are given in degrees centigrade and are uncorrected. The $[\alpha]_D^{20}$-values are also uncorrected.

EXAMPLE 1

3-(4-(2-Ethylphenyl)-2-carboxamido-indole)-D-alanine a) 4-(2-Ethylphenyl)-indole-2-carboxylic acid To a mixture of 0.28 g of 4-bromo-indole-2-carboxylic acid and 0.069 g of tetrakistriphenylphosphinepalladium in 11 ml of toluene and 2 ml of 2M soda is added a solution of 0.300 g of 2-ethylphenylboronic acid in 3 ml of ethanol. This mixture is refluxed for 16 h, filtered and the aqueous phase acidified with 2N HCl and extracted with ethyl acetate. Concentration of the organic phase gives the product as a brownish powder, m.p. 230-233°, sufficiently pure for the next step.

b) 3-(4-(2-Ethylphenyl)-2-carboxamido-indole)-N(2)-Z-D-alanine methylester

To a solution of 2.11 g of 4-(2-ethylphenyl)-indole-2-carboxylic acid in 32 ml of pyridine are added 1.41 g of carbonyldiimidazole. After termination of the gas evolution, 2.29 g of methyl N(2)-Z-D-2,3-diaminopropionate are added and the mixture stirred at room temperature for 4 days. After evaporation of the solvent the residue is extracted with water/ethyl acetate, the organic phase dried, concentrated and the crude product chromatographed on silica with isopropyl acetate/toluene 4:1, yielding the desired compound as a yellow amorphous powder.

c) 3-(4-(2-Ethylphenyl)-2-carboxamido-indole)-D-alanine

A mixture of 2.03 g of 3-(4-(2-ethylphenyl)-2-carboxamido-indole)-N(2)-Z-D-alanine methyl ester, 4.1 ml of 2N NaOH and 10 ml of dioxane is stirred at room temperature for 2 h. After working up in conventional manner the obtained acid is dissolved in 22 ml of methylene chloride and treated with 1.03 ml of iodotrimethylsilane at 0° C. After stirring for 50 min. the mixture is concentrated to dryness and the residue taken up in water. The crude product precipitates out and is collected by filtration, washed with water and recristallised from water/isopropanol under adjustment of the pH to 6 by addition of 0.2N NaOH, yielding the title compound as a white powder, m.p. 258-265°.

The compounds of formula I wherein $R_1$ and $R_2$ are as defined in Table 1, may be prepared by following one of the above procedures but using the appropriate starting materials.

TABLE 1

| Ex. | $R_1$ | $R_2$ | Melt. Point (° C.) |
|---|---|---|---|
| 2 | 2-benzyl-phenyl | H | 220 |
| 3 | naphthalen-2-yl | H | 226-233 |
| 4 | naphthalen-1-yl | H | 210 |
| 5 | 2-ethyl-phenyl | $CH_3$ | 220 |
| 6 | 2-butoxy-phenyl | H | 210-220 |
| 7 | 2-propyl-phenyl | H | 245 |
| 8 | 2-isopropyl-phenyl | H | 245-260 |
| 9 | 2,4-dichloro-phenyl | H | 235 |

The compounds disclosed herein which are selective S1P4 receptor agonists (hereinafter referred to as the compounds of the invention), e.g. the compounds of formula I, in free form or in pharmaceutically acceptable salt form, exhibit valuable pharmacological properties, e.g. lymphocyte recirculation modulating properties, e.g. as indicated in in vitro and in vivo tests and are therefore indicated for therapy. In particular, the compounds of the invention are useful as functional agonists of human S1P4 (EDG6) receptors, as demonstrated in the following assays.

Assays to Determine the in Vitro Pharmacology of the S1P4 Compounds a) Expression Vector Encoding Human S1P Receptors An expression vector for the human S1P4 gene (HSEDG4; GenBank Accession Number AJ000479) fused to the c-myc peptide tag at the C-terminus is obtained as described in Van Brocklyn et al. 2000, Blood 95(8), 2624. The encoding DNA for the S1P4-myc fusion protein is cloned in the mammalian expression vector pRc/CMV (Invitrogen), which confers G418 resistance for the selection of stable mammalian cells. The DNA sequence of the S1P4 insert is determined on both strands. No nucleotide differences are found that would lead to amino acids changes as compared with the GenBank entry for HSEDG4. The S1P4-myc cDNA is inserted into the pRc/CMV vector using HindIII/XbaI.

Following vectors are used.

Human S1P1 (GenBank™ accession number M31210) and S1P3 (GenBank™ accession number X83864) cDNA containing the myc sequence in front to the human S1P1 and S1P3 sequences are inserted in the pcDNA 3.1 vector. The vectors are sequenced to completion to confirm the correctness of the construct. The human S1P2 (GI: 4090955, TREMBL: O195136) is cloned by a PCR based method. Lung cDNA (marathon cDNA) is obtained (BD Biosciences Chontech, Palo Alto, Calif. 94303, USA). Following oligonucleotides are used for the PCR reaction: forward primer CAC CAT GGG CAG CTT GTA CTC GGA GTA CCT GM CCC CAA CM GGT CCA G (1 to 45, GenBank™ accession number AF034780) and reverse primer 5'-GAT TCA GAC CAC CGT GTT GCC CTC CAG (1062 to 1039, GenBank™ accession number AF034780), the initiation of the translation (ATG) and the stop codon are underlined. The PCR is performed in the presence of 0.2-0.4 µg cDNA, 1× reaction buffer (10× PfuTurbo DNA polymerase buffer, Stratagene, La Jolla, Calif. 92037, USA), 0.5 µM primers, 0.25 mM dNTP's and 2.5 units PfuTurbo DNA polymerase (Stratagene), a first step at 95° C. for 2 min, 30 cycles (30 sec at 95° C., 30 sec at 60° C. and 90 sec at 72° C.) and final step of 10 min at 72° C. The amplified product of around 1100 bp is analyzed by standard agarose gel-electrophoresis. After the cloning of the PCR product in the pcDNA 3.1 Topo V (Invitrogen Corporation) the DNA inserts from different bacterial colonies are sequenced. The final sequence is assembled from three independent plasmid preparations that are sequenced in both directions.

The human S1P5 (GI: 30171332 or GenBank™ accession number AY262689, TREMBL: Q9H228) is cloned by a PCR based method. Lung and spleen cDNA (marathon cDNA) is obtained from BD Biosciences Chlontech (BD Biosciences Chlontech, Palo Alto, Calif. 94303, USA); genomic DNA is isolated from HeLa cells using standard procedures. Following oligonucleotides are used for the PCR reaction: forward primer CAC CATGGA GTC GGG GCT GCT GCG (−4 to 20, GenBank™ accession number AY262689) and reverse primer 5'-TCA GTC TGC AGC CGG TTC TGA TAC CAG AGT C (1197 to 1131, AY262689), the initiation of the translation (ATG) and the stop codon are underlined. The PCR is performed In the presence of 0.2-0.4 µg cDNA, 1× reaction buffer (10× PfuTurbo DNA polymerase buffer, Stratagene, La Jolla, Calif. 92037, USA), 0.5 µM primers, 0.25 mM dNTP's and 2.5 units PfuTurbo DNA polymerase (Stratagene), a first step at 95° C. for 2 min, 30 cycles (30 sec at 95° C., 30 sec at 60° C. and 90 sec at 72° C.) and final step of 10 min at 72° C. The amplified product of around 1100 bp is analyzed by standard agarose gel-electrophoresis. After the cloning of the PCR products in the pcDNA 3.1 Topo V (Invitrogen Corporation) the DNA inserts from different bacterial colonies are sequenced. The final sequence is assembled from three independent plasmid preparations that are sequenced in both directions.

b) Development of a CHO-K1 Cell Line Stably Expressing S1P4

To develop stable cell lines expressing the c-myc tagged S1P4 receptor 5 µg of plasmid pRc/CMV myc-S1P4 is cut using restriction endonuclease PvuI, which cleaves the plasmid once. The linearized plasmid is then precipitated using a final concentration of 0.3M sodium acetate, pH5.0 and 66% ethanol. After centrifugation and washing, the DNA pellet is dissolved in 30 µl water. For transfection, CHO-K1 (ATCC Number: CCL-61) cells are plated in MEM a medium (minimum essential medium alpha modification) containing 10% FCS (fetal calf serum) the day before transfection at a cell density of $1 \times 10^6$ cells per well of 100-mm cell culture dish (Falcon) and incubated at 37° C. in a 5% $CO_2$ atmosphere for 24 hours. At the day of transfection, 5 µg of linearised pRC/CMV myc-S1P4 plasmid are added to 270 µl of RPMI medium. After adding 60 µl of SuperFect Transfection Reagent (Qiagen) to the DNA solution and mixing for 10 seconds, the sample is incubated for 10 min to allow complex formation. The DNA-SuperFect complex is mixed with an additional 3 ml of RPMI/10% FCS and then transferred to the cell monolayer. After 3 hours of incubation, the transfection medium Is removed and the cells washed with PBS. Fresh RPMI medium supplemented with 10% FCS is added and cells incubated for 72 hours at 37° C. and 5% $CO_2$. Selection for stable transformed clones is performed after adding 500 µg/ml G418 (Lifetechnologies). After about 12-14 days, cell clones obtained by sorting single cells according to their forward and sideward scatter characteristics into Individual wells of a 96-well cell culture plate using a FACStar Plus cell sorter (BectonDickinson). Individual clones that grew after the sort and selection procedure are expanded and one clone is finally selected based on the level of S1P4 mRNA expression determined by TaqMan quantitative PCR analysis.

c) Cell Culture Maintenance

Parental CHO-K1 cells are maintained in RPMI medium (Lifetechnologies), supplemented with 10% FBS and 10 µg/ml gentamicin (Lifetechnologies). S1P4/myc transfected CHO-K1 cells, including the one finally selected clone are maintained in MEM alpha medium, supplemented with 10% FBS, 10 µg/ml gentamicin and 0.5 mg/ml G418 (Lifetechnologies).

d) Determination of S1P4 Transcription Levels in CHO Stable Clones

Total RNA from cells is isolated with the help of the RNeasy Mini kit (Qiagen). After the disruption of cells (grown in a monolayer) directly in culture dishes (for one 35 mm dish, 350 µl buffer are used, prepared according to the protocol of Qiagen), the lysate is pipetted onto a qiashredder spin column and centrifuged for 2 min at 21,000×g. 350 µl of 70% ethanol are added to the flow-through, mixed well, applied to an RNeasy mini column, and centrifuged for 15 sec at 10,000×g. The flow-through is discarded, 700 µl buffer RW1 (Qiagen) are added to the RNeasy column and centrifuged for 15 sec to rinse the column. The column is further washed by adding twice 500 µl Buffer RPE (Qiagen) and centrifuging for 15 sec at 10000×g. The RNA is eluted by adding in 30-50 µl RNAse-free water directly onto the RNeasy column and centrifuging for 1 min at 10,000×g The RNA is reverse-transcribed with the Omniscript kit of Qiagen (Qiagen). Around 2 µg RNA are mixed with 2 µl 10× buffer, 2 µl dNTP Mix, 1 µl RNase inhibitor (10 units/µl), 0.5 µg random hexamer, 1 µl Omniscript Reverse Transcriptase and RNase-free water to a final volume of 20 µl, and incubated at 37° C. for 60 min and additional 30 min at 42° C. The reaction is inactivated for 5 min at 93° C., cooled on ice and stored at −20° C. until used.

To determine the relative transcription levels of S1P4 mRNA in the selected clones, real time PCR (polymerase chain reaction) analysis is performed. Optimal primer and probe concentrations are determined as described in the User bulletin provided by PE (Perkin/Elmer) Biosystems using a human S1P4 containing plasmid as a template. The human S1P4 oligonucleotides as well as their optimized concentrations for real-time PCR are following (based on HSEDG4; GenBank Accession Number AJ000479):

| Primer/Probe | label | Sequence | Opt.conc |
|---|---|---|---|
| Forward Primer | none | AACTGCCTGTGCGCCTTT | 50 nM |
| Reverse Primer | none | GAGGATGTAGCGCTTGGAGTAGA | 900 nM |
| Probe | 5'-FAM, 3'TAMRA | ACCGCTGCTCCAGCCTTCTG | 100 nM |

First strand cDNA is then used for quantitative PCR on the ABI7700 TaqMan machine (PE Biosystems). As an internal control of the amount of RNA present in each sample, 18S ribosomal RNA is used by multiplexing the S1P4 PCR reaction with the ribosomal RNA PCR In the same tube using the TaqMan Ribosomal RNA control reagents (PE Biosystems, P/N4308310, VIC-labeled probe). Although similar efficiency of the two independent amplifications for S1P4 and ribosomal RNA is not formally determined, the semi-quantitative determination of the S1P4 transcription levels in the different cell clones is sufficient for the selection of cell clones to be further characterized in functional assays.

e) Preparation of Membranes

Membrane proteins are prepared from wild type CHO-K1 and the CHO cell clones expressing human S1P4. To obtain 10-30 mg of membrane proteins, cells are grown in one large culture dish (500 cm$^2$) per cell clone to 80 and 90% confluence. The culture medium is removed and the cells are harvested on ice from the dish, by scraping in 20 ml cold HEPES 10 mM (pH 7.5) supplemented with 0.1% fatty acid-free bovine serum albumin (BSA) and protease inhibitors cocktail (one tablet per 50 ml, Roche Diagnostics, Rotkreuz). The cells are centrifuged at 750×g for 10 min at 4° C. and re-suspended in 10 ml cold membrane buffer (20 mM HEPES, pH 7.4; 100 mM NaCl; 10 mM MgCl$_2$; 1 mM EDTA; 0.1% BSA and protease inhibitors cocktail). The cell suspension is homogenized on ice, using a Polytron homogenizer at 25000 rpm at three intervals of 20 seconds each. The homogenate is centrifuged at 26,900×g for 30 min. at 4° C. and the membrane protein pellet resuspended by vortexing in 2 ml of cold membrane buffer. The protein concentration is determined using the Bio Rad Protein Assay and human IgG as standard. The volume of the membrane protein suspension is adjusted to result in a final concentration of 2 to 3 mg protein/ml. The solution is then once again homogenized (Polytron) on ice at 25000 rpm for 20 sec before to be aliquoted into Eppendorf tubes at the volume of 0.8-1 ml.

f) Activity Measurements of the Cells Expressing hS1P4:

f1) GTPγ$^{35}$S Binding Assay

The selection of the clones to be tested in the GTPγS assay is based on the real time PCR assays. CHO clones expressing large amounts of human S1P4 are used in these experiments. Membrane proteins are prepared as described above. The basic protocol of GTPγ$^{35}$S-binding assay used is described in a recent publication (Brinkmann et al. 2002, J. Biol. Chem, 277, 21453) with the modifications described here below. To characterize the GTPγ$^{35}$S-binding to membrane proteins from CHO cells expressing S1P, WGA coated PVT beads (SPA-bead, Amersham Biosciences) are used. Because β-rays of GTPγ$^{35}$S have significant penetration in water solution, the plates are centrifuged to minimize non-specific effects caused by the non bound GTPγ$^{35}$S. The assay is performed in 96-well Optiplates (Packard, Cat. N° 6005190) in final volume of 225 µl/well. After a short homogenization, the membrane proteins are resuspended at different concentrations (between 25 to 150 µg/ml) in 50 mM HEPES, 100 mM NaCl, 10 mM MgCl$_2$, 20 µg/ml saponin (Riedel-de-Haen: Cat. N° 16109), 0.1% fat free BSA (Sigma Cat. N° A0281) pH 7.4. The membrane proteins are mixed with 1 mg/well SPA-bead, 10 µM GDP, different concentrations of agonists and incubated for 10-15 min at RT. The GTPγ$^{35}$S binding reaction is started by the addition of 200 µM GTPγ$^{35}$S (Amersham, Cat. No SJ13O8, >1000 Ci/mmol). The Optiplates are sealed and incubated at RT for 110-120 minutes with constant shaking. The plates are then centrifuged for 10 minutes at 2000 rpm and counted with a TopCount instrument (Packard). Calculations of the EC$_{50}$ are performed with a non-linear regression fit program as available in the Origin 7 RS2 software package (Origin Lab Corporation, One Roundhouse Plaza, Northampton, Mass. 01060, USA).

f2) Calcium mobilization assay

CHO cells are plated in black Costar plate (96 or 384 well, 50,000 cells or 12,500 cells, respectively) in a MEM with FCS and cultured for 20-24 h at 37° C. in a CO$_2$ incubator. After the removal of the culture medium cells are incubated in HBSS medium containing 2 µM Fluo4AM (Molecular Probes, Cat. No, F-1241; 1 mg/ml stock in DMSO), 5 mM probenicid for 1 h at 37° C., rinsed with HBSS buffer, 2.5 mM probenicid and overlaid with the same medium (75 µl for 96-well plates, 50 µl for 384 plates). The plates are transferred to the FLIPR. After measuring the baseline for 40 sec, the agonist in HBSS is added and the fluorescence is measured at intervals of 2 sec for 3 to 5 min. In some cases the cells are pre-treated for 5 h with 50 ng/ml pertussis toxin (Sigma, Cat Nr P2980). 2-aminoethoxydiphenyl borate (2-APB, Calbiochem, Juro Supply, Bleicherstr. 11, Lucerne, Switzerland, Cat Nr 100065) a blocker of the release of calcium from the endoplasmic reticulum (Ascher-Landsberg et al., 1999, Biochem. Biophys. Res. Commun. 264, 979) at 50 µM and/or 150 µM is added directly to the cell medium 20-40 min prior to the measurements. Calculations of the EC$_{50}$ are performed using a non linear regression fit program provided in the Origin 7 RS2 software package (Origin LabCorporation) available to Novartis.

In Vitro Determination of the Specificity and Selectivity of the S1P4 Agonists:

The compounds mentioned in this application are tested for specificity, e.g. the activity they have in the parental cell line prior transformation with the S1P4 cDNA and for selectivity on CHO cells lines transformed with the S1P1, S1P2, S1P3, and S1P5. The generation of stable cell lines for the other S1P receptors is done as described for S1P4, using published human cDNA sequences as described above. Preferably compounds with a selectivity and specificity of 100× are chosen. For example, S1P4 specific and selective compounds may have an EC$_{50}$ (apparent EC$_{50}$) measured at S1P4 that is 10×, preferably 100× lower that that measured in wild type CHO cells or In cell expressing any of the other four S1P receptors.

For example if an $EC_{50}$ of 200 nM is measured for S1P4, the $EC_{50}$'s in CHO cells or in CHO cells expressing S1P1, 2, 3, 5 is preferably $\geq 20$ μM. The compound of example 1 has an $EC_{50}$ for S1P4 in this assay of 432 nM.

The $EC_{50}$ values (in μM) for the compound of example 2 in CHO cells or in CHO cells expressing various S1P receptors is shown in Table 2 below:

TABLE 2

|  | CHO | S1P1 | S1P2 | S1P3 | S1P4 | S1P5 |
| --- | --- | --- | --- | --- | --- | --- |
| Calcium mobilization assay | >6 | >6 | >6 | >6 | 0.01 | 2.4 |
| GTPγS binding assay | >10 | >10 | >10 | >10 | 0.25 | >10 |

The compounds of the invention are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, others, cancer, e.g. T cell lymphomas or T cell leukemias, infectious diseases, e.g. toxic shock (e.g. superantigen induced), septic shock, adult respiratory distress syndrome or viral infections, e.g. AIDS, viral hepatitis or chronic bacterial infection. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

For the above uses the required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of the invention may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of the invention in free form or in pharmaceutically acceptable salt form in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of the invention, e.g. a compound of formula I, or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of the invention, e.g. a compound of formula I, or a pharmaceutically acceptable salt thereof;

2. A compound of the invention, e.g. a compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of the invention, e.g. a compound of formula I, in free form or pharmaceutically acceptable salt form in association with a pharmaceutically acceptable diluent or carrier therefor.

The compounds of the invention, e.g. a compound of formula I, may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of the invention may be used in combination with a calcineurin inhibitor, e.g. cyclosporin A or FK 506; a mTOR inhibitor, e.g. rapamycin, 40-O-(2-hydroxyethyl)-rapamycin, CCI779 or ABT578; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil.

Where the compounds of the invention, e.g. a compound of formula I, are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

4. A method as defined above comprising co-administration, e.g. concomitantly or in sequence, of a therapeutically effective non-toxic amount of a compound of the invention, e.g. a compound of formula I and at least a second drug substance, e.g. an immunosuppressant, immunomodulatory, anti-inflammatory or chemotherapeutic drug, e.g. as indicated above.

5. A pharmaceutical combination, e.g. a kit, comprising a) a first agent which is a compound of the invention, e.g. a compound of formula I, as disclosed herein, in free form or in pharmaceutically acceptable salt form, and b) at least one co-agent, e.g. an immunosuppressant, immunomodulatory, anti-inflammatory or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:

1. A compound of formula I

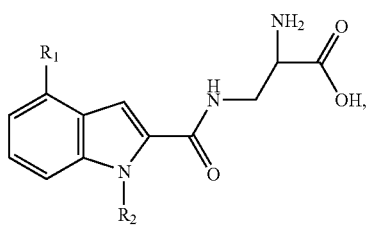

wherein $R_1$ is phenyl or naphthyl, where phenyl is substituted by one or two of halogen, $C_{1-6}$-alkyl, $C_{1-6}$-alkoxy or phenyl-$C_{1-6}$-alkyl; and $R_2$ is hydrogen or $C_{1-6}$-alkyl;

in free or salt form.

2. A compound according to claim 1 that is selected from 3-(4-(2-ethylphenyl)-2-carboxamido-indole)-alanine, 3-(4-(2-benzyl-phenyl)-2-carboxamido-indole)-alanine, 3-(4-(naphtalen-2-yl)-2-carboxamido-indole)-alanine, 3-(4-(naphtalen-1-yl)-2-carboxamido-indole)-alanine, 3-(4-(2-butoxy-phenyl)-2-carboxamido-indole)-alanine, 3-(4-(2-propyl-phenyl)-2-carboxamido-indole)-alanine, 3-(4-(2-isopropyl-phenyl)-2-carboxamido-indole)-alanine, 3-(4-(2,4-dichloro-phenyl)-2-carboxamido-indole)-alanine, and pharmaceutically-acceptable salts thereof.

3. A compound according to claim 1 that is 3-(4-(2-ethylphenyl)-2-carboxamido-indole)-D-alanine, in free form or in a pharmaceutically-acceptable salt form.

4. A pharmaceutical composition comprising a compound according to claim 1, in free form or in pharmaceutically-acceptable salt form, in association with a pharmaceutically-acceptable diluent or carrier.

5. A pharmaceutical combination comprising a compound according to claim 1 in free form or in a pharmaceutically-acceptable salt form and a further agent selected from immunosuppressant, immunomodulatory, anti-inflammatory and chemotherapeutic drug agents.

6. A process for the production of the compound according to claim 1, which process comprises deprotecting a compound of formula II:

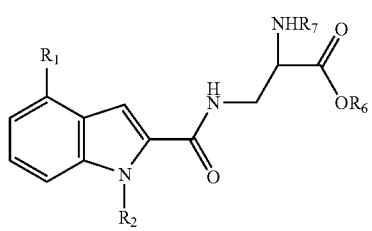

wherein $R_1$ and $R_2$ are as defined in claim 1, $R_6$ is $C_{1-6}$alkyl or benzyl, $R_7$ is an amino protecting group, and optionally converting the compound of formula I obtained in free form to a salt form or vice versa.

7. A method for treating acute or chronic transplant rejection comprising administering to a subject an effective amount of a compound according to claim 1, or a pharmaceutically acceptable salt thereof.

\* \* \* \* \*